United States Patent [19]

Cragle et al.

[11] Patent Number: 4,595,661
[45] Date of Patent: Jun. 17, 1986

[54] IMMUNOASSAYS AND KITS FOR USE THEREIN WHICH INCLUDE LOW AFFINITY ANTIBODIES FOR REDUCING THE HOOK EFFECT

[75] Inventors: Linda K. Cragle, San Diego; Paul C. Harris, Yorba Linda; Shih-Yun Lee, San Marcos; Ker-Kong Tung, Carlsbad; Morton A. Vodian, Escondido, all of Calif.

[73] Assignee: Beckman Instruments, Inc., Fullerton, Calif.

[21] Appl. No.: 553,219

[22] Filed: Nov. 18, 1983

[51] Int. Cl.$^4$ ............... G01N 33/546; G01N 33/53; G01N 33/543; C12Q 1/00
[52] U.S. Cl. ............... 436/534; 435/4; 435/7; 435/810; 436/513; 436/518; 436/531; 436/533; 436/536; 436/538; 436/548; 436/805; 436/808; 436/818; 436/819
[58] Field of Search ............... 436/513, 518, 531, 534, 436/536, 538, 548, 805, 808, 818, 819, 533; 435/4, 7, 810

[56] References Cited

U.S. PATENT DOCUMENTS

| | | | |
|---|---|---|---|
| 4,115,535 | 9/1978 | Giaever | 436/526 |
| 4,184,849 | 1/1980 | Cambiaso et al. | 436/523 |
| 4,223,005 | 9/1980 | Teodorescu et al. | 436/519 |
| 4,279,617 | 7/1981 | Masson et al. | 436/509 |
| 4,305,925 | 12/1981 | Kapmeyer et al. | 436/509 |
| 4,308,026 | 12/1981 | Mochida et al. | 436/520 |
| 4,361,647 | 11/1982 | Remington et al. | 435/7 |
| 4,376,110 | 3/1983 | David et al. | 436/513 |

OTHER PUBLICATIONS

Anido, "Clin. Chem." 30:500 (1982).
Revenant et al., "Clin. Chem." 28:253, (1982).
Ehrlich et al., "J. of Immunol." 128(6), pp. 2709–2713, (1982).

Primary Examiner—Sidney Marantz
Assistant Examiner—Patricia Kate White
Attorney, Agent, or Firm—W. H. May; A. Grant; R. S. Friedman

[57] ABSTRACT

An immunoassay for assaying an antigenic substance (Ag) in a fluid. The immunoassay is the type which comprises contacting the fluid with at least one first entity selected from a group consisting of an antibody (Ab) to the Ag, a soluble, labeled antibody (L-Ab$_a$) to the Ag, and an antibody (Ab$_b$) to the Ag bound to a solid support (SC). The immunoassay is characterized in that the fluid is contacted with at least one additional entity selected from a group consisting of at least one different type of soluble, labeled antibody (L-Ab$_c$) to the Ag, at least one different type of antibody (Ab$_d$) bound to a solid carrier (SC$_1$), and at least one different type of antibody (Ab$_e$) to the Ag. The SC$_1$ is selected from a group consisting of SC, at least one different solid carrier (SC$_2$), and mixtures thereof (SC and SC$_2$). Each type of L-Ab$_c$, Ab$_d$-SC$_1$, and Ab$_e$ has a lower average affinity constant (K) for Ag than each respective K of L-Ab$_a$, Ab$_b$-SC and Ab$_e$; and the additional entity is present in an amount sufficient to avoid a hook effect.

Also, a reagent of the type comprising at least one first entity selected from a group consisting of L-Ab$_a$, Ab$_b$-SC, and Ab. The reagent is characterized in that it further comprises at least one additional entity selected from a group consisting of at least one different type of L-Ab$_c$ and at least one different type of Ab$_d$-SC$_1$, and at least one different type of Ab$_e$. Ab, L-Ab$_a$, Ab$_b$-SC, L-Ab$_c$, Ab$_d$-SC$_1$, and Ab$_e$ are as defined above.

20 Claims, No Drawings

1

IMMUNOASSAYS AND KITS FOR USE THEREIN WHICH INCLUDE LOW AFFINITY ANTIBODIES FOR REDUCING THE HOOK EFFECT

BACKGROUND OF THE INVENTION

1. Field of the Invention

This invention relates to immunoassays and to kits for use therein.

2. Description of the Prior Art

Numerous types of immunoasays presently exist. To illustrate, one- and two-step sandwich immunoassays for antigens which combine to at least two antibodies are known (1-4). For example, U.S. Pat. No. 4,244,940 (2) discloses a sandwich immunoassay method in which a sample containing an antigen (Ag) to be determined, a labeled antibody (L-$Ab_a$) to the Ag, an antibody ($Ab_b$) for the Ag bound to a solid-phase support (SC) are brought together in a single incubation mode or step in an aqueous medium to form a substantially stable suspension and produce a two-phase system. The solid phase portion of this two-phase system contains the $Ab_b$-SC, a portion of which has become bound to the Ag which in turn has become bound to a portion of the L-$Ab_a$ (represented as L-$Ab_a$-Ag-$Ab_b$-SC). The liquid phase portion of the two-phase systems contains the unbound portion of the L-$Ab_a$. The solid and liquid phases are separated and either phase analyzed for the L-$Ab_a$, the concentration of which is a function of the concentration of Ag in the sample. U.S. Pat. No. 4,244,940 (2) teaches that this two-site immunoassay employing a single incubation mode or step provides significant advantages over assay procedures involving more than one incubation by simplifying, shortening, and rendering more convenient the performance of the assay. Furthermore, U.S. Pat. No. 4,244,940 (2) teaches that this improvement in assay procedure is accomplished while maintaining acceptable assay characteristics such as precision, specificity, and stability, in addition to being less subject to errors in timing, additions, and other manipulations.

One- and two-step sandwich immunoassays, can be used for the determination of the presence or concentration of any Ag which can simultaneously become bound by two antibodies. This group of Ags includes, but is not limited to, placental, pituitary, calcium regulating, and adrenal medullary polypeptide hormones, protein and protein fragments; immunoglobulins (antibodies) of various classes; viral, viral subunits, bacterial, and protozoal organisms or particles; toxins; drugs, enzymes, and tumor-associated antigens.

In the one- and two-step sandwich immunoassays, the antibody employed is any substance which binds the Ag with acceptable specificity and affinity.

In one- and two-step sandwich immunoassay the L-$Ab_a$ may be labeled with any of a number of known tracers. These tracers include, but are not limited to, radioactive tags, fluorescent labels, and enzyme labels.

An important component of the one- and two-step sandwich immunoassays is the SC for the $Ab_b$. The SC must be able to (a) be bound to the $Ab_b$, (b) be handled conveniently during manipulations such as pipetting and centrifuging, and (c) exhibit low nonspecific adsorption properties or be treated so that it exhibits such adsorption properties.

A pitfall in both the conventional and one-step sandwich immunoassay has been reported (3,5-7). More particularly, these authors have found that a potential hazard of misinterpreting the results is involved in both the conventional and one-step sandwich immunoassays because of a false negative result or "hook effect" at high concentrations of Ag.

Nomura et al. (6), who discuss this pitfall in regard to a one-step sandwich immunoassay with monoclonal antibodies for the determination of human alphafetoprotein (AFP), state that "theoretically but not practically, the inhibition in antigen excess region may be avoided by employing a large amount of immobilized and labeled anti-AFP." One reason that this suggestion is not practical is that the additional large amount of labeled anti-AFP suggested by Nomura et al. would result in an assay having high non-specific adsorption since non-specific adsorption is proportional to the concentration of L-$Ab_a$ employed. Another reason that this suggestion is not practical is that this additional large amount of labeled anti-AFP would reduce the dynamic range of the assay when an enzyme or other label requiring the use of a spectrophotometer is employed.

Miles et al. (7), who discuss this pitfall in regard to a two-step sandwich immunoassay, note that repeated washings after the first incubation does prevent the high dose hook effect. However, this technique for preventing the high dose hook effect is tedious and time consuming.

To date, there has been no convenient technique proposed for either preventing or avoiding this false negative or hook effect phenomenum in either one- or two-step sandwich immunoassays.

Another immunoassay known to those skilled in the art is the direct nephelometric immunoassay. The direct nephelometric immunoassay comprises contacting a fluid containing an antigenic substance (Ag) with an antibody (Ab) to the Ag in order to form a complex Ab-Ag. A measurement of the amount of formed Ab-Ag is directly proportional to the amount of Ag in the assayed fluid.

Like the one- and two-step sandwich immunoassays, there is a potential hazard of misinterpreting the results because of the false negative result or "hook effect" at high concentrations of Ag.

Although in the case of the direct nephelometric immunoassay there are some electromechanical methods for safeguarding against such misinterpretation, at present there is no known chemical means for either preventing or avoiding this false negative or hook effect phenomenon in this case either.

Accordingly, it would be very desirable to have immunoassay methodologies and kits wherein this problem has been either prevented or avoided.

SUMMARY OF THE INVENTION

In accordance with the present invention, there are provided improved immunoassay methodologies and kits for use therein wherein all the advantages possessed by the prior immunoassays are maintained with the concurrent avoidance of the hook effect.

In general, the present invention encompasses an improved immunoassay for an antigenic substance (Ag) in a fluid. The immunoassay of the present invention is of the type which comprises contacting the fluid with at least one first entity selected from a group consisting of an antibody (Ab) to the Ag, a soluble, labeled antibody (L-$Ab_a$) to the Ag, and an antibody ($Ab_b$) to the Ag bound to a solid carrier (SC). The present immunoassay is characterized in that the fluid is contacted with at least one additional entity selected from a group consisting of at least one different type of soluble, labeled antibody (L-$Ab_c$) to the Ag, at least one different type of antibody ($Ab_d$) to the Ag bound to a solid carrier ($SC_1$), and at least one different type of antibody ($Ab_e$) to the Ag.

$SC_1$ is selected from a group consisting of SC, one or more different solid carriers ($SC_2$), and mixtures thereof (SC and $SC_2$).

Each of the additional entities has an average affinity constant (K) for the Ag lower than the K of its corresponding first entity for the Ag. In addition, the additional entity is present in an amount sufficient to avoid the hook effect.

More particularly, the present invention encompasses an improved one-step sandwich immunoassay. This one-step sandwich immunoassay of the present invention is of the type which comprises:

(a) contacting the fluid with (i) the L-$Ab_a$ and (ii) the $Ab_b$ bound to the SC to form an insoluble complex (L-$Ab_a$-Ag-$Ab_b$-SC);

(b) separating the L-$Ab_a$-Ag-$Ab_b$-SC from the fluid and unreacted L-$Ab_a$; and (c) measuring either the amount of L-$Ab_a$ associated with the L-$Ab_a$-Ag-$Ab_b$-SC or the amount of unreacted L-$Ab_a$.

The improved one-step sandwich immunoassay of this invention is characterized in that the fluid is contacted with at least one additional entity selected from the group consisting of one or more different type of L-$Ab_c$ and one or more different type of $Ab_d$ bound to the $SC_1$; wherein:

(i) each different type of L-$Ab_c$ and $AB_d$-$SC_1$ has a lower K for Ag than each respective K of L-$Ab_a$ and $Ab_b$-SC for Ag; and (ii) the additional entity is present in an amount sufficient to avoid the hook effect.

More particularly, the present invention also encompasses an improved two-step sandwich immunoassay. This immunoassay is of the type which comprises:

(a) contacting the fluid containing the Ag with the $Ab_b$-SC to form an insoluble complex (Ag-$Ab_b$-SC);

(b) contacting the Ag-Ab-SC with the L-$Ab_a$ to form an extended insoluble complex (L-$Ab_a$-Ag-$Ab_b$-SC);

(c) separating the L-$Ab_a$-Ag-$Ab_b$-SC from unreacted L-$Ab_a$; and (d) measuring either the amount of L-$Ab_a$ associated with the L-$Ab_a$-Ag-$Ab_b$-SC or the amount of unreacted L-$Ab_a$.

The improved two-step sandwich immunoassay of this invention is characterized in that in step (b) the Ag-$Ab_b$-SC is contacted with one or more different type of L-$Ab_c$, wherein each different type of L-$Ab_c$ has a lower K for Ag than the K of L-$Ab_a$ and L-$Ab_c$ is present in an amount sufficient to avoid the hook effect.

More particularly, the present invention also encompasses an improved direct nephelometric immunoassay. This immunoassay is of the type which comprises:

(a) contacting the fluid with Ab in order to form a complex Ab-Ag; and (b) measuring the amount of formed Ab-Ag.

The improved direct nephelometric immunoassay of this invention is characterized in that the fluid is contacted with at least one additional type of antibody $Ab_e$. Each type of $Ab_e$ has a K for the Ag lower than the K of the Ab for the Ag and is present in an amount sufficient to avoid the hook effect.

Also within the general scope of this invention is an improved reagent. This improved reagent is of the type comprising at least one first entity selected from a group consisting of Ab, L-$Ab_a$, and $Ab_b$-SC. The reagent of the present invention is characterized in that it further comprises at least one additional entity selected from a group consisting of at least one different type of L-$Ab_c$, at least one different type of $Ab_d$-$SC_1$, and at least one different type of $Ab_e$. The additional entity is present in an amount sufficient to avoid a hook effect when the reagent is employed in an immunoassay.

In the case of one- and two-step sandwich immunoassays, the reagent is of the type comprising L-$Ab_a$ and $Ab_b$-SC. The improved reagent of the present invention is characterized in that it further comprises at least one additional entity selected from a group consisting of one or more different types of L-$Ab_c$ and one or more different types of $Ab_d$ bound to $SC_1$. The additional entity is present in an amount sufficient to avoid the hook effect when the reagent is employed in the immunoassay.

In the case of direct nephelometric immunoassays, the reagent is of the type comprising Ab. The improved reagent of the present invention further comprises at least one different type of $Ab_e$ in an amount sufficient to avoid the hook effect when employed in a direct nephelometric assay.

DESCRIPTION OF THE PREFERRED EMBODIMENTS

The average affinity constant (K) for each different type of L-$Ab_c$, $Ab_d$-$SC_1$, and $Ab_e$ for Ag must be lower than each respective K of L-$Ab_a$, $Ab_b$-SC and Ab for Ag. This restriction assures that the former entities compete at most only insignificantly with the latter entities in the dynamic range. In order to acheive this result, it is preferred that each K of each different type of L-$Ab_c$, $Ab_d$-$SC_1$, and $Ab_e$ for Ag be at least 5, more preferably at least 10 times lower than each respective K of L-$Ab_a$, $Ab_b$-SC, and Ab for Ag.

In addition, the further one wishes to extend the avoidance of the hook effect, the larger the difference must be between (a) the K of L-$Ab_a$ and the K of L-$Ab_c$, (b) the K of $Ab_b$-SC and the K of $Ab_d$-$SC_1$, and (c) the K of Ab and the K of $Ab_e$.

When more than one type of L-$Ab_c$, $Ab_d$-$SC_1$, or $Ab_e$ is employed, each different type preferably has a different K.

The amount of L-$Ab_c$ employed can be any amount sufficient to extend the commencement of the hook effect and up to that which gives unsatisfactory nonspecific adsorption. More particularly, this amount can range from about 0.01 to about 1 μg per ml of reagent.

The amount of $Ab_d$ employed can be any amount sufficient to extend the commencement of the hook effect and up to the amount required to saturate $SC_1$. More particularly, this amount can range from 0.1 to about 10 μg per test.

The amount of $Ab_e$ employed can be any amount sufficient to extend the commencement of the hook effect.

In order to obtain the advantages of the present invention in a one- or two-step sandwich immunoassay, one need only employ either L-$Ab_c$ or $Ab_d$-$SC_1$. Since it is easier to adjust the labeled antibody concentration and since it is also easier to adjust the ratio of L-$Ab_a$ to L-$Ab_c$, it is preferred to only employ L-$Ab_c$ as the additional entity.

$Ab_a$, $Ab_b$, $Ab_c$, $Ab_d$, and $Ab_e$ are each independently selected from a group consisting of monoclonal antibodies, polyclonal antibodies, and mixtures thereof. For example, in one- and two-step sandwich immunoassays, (a) $Ab_a$, $Ab_b$, $Ab_c$, and $Ab_d$ can be monoclonal antibodies or can be polyclonal antibodies; or (b) $Ab_a$ and $Ab_c$ can be both monoclonal antibodies and $Ab_b$ and $Ab_d$ can be both polyclonal antibodies; or (c) $Ab_a$ and $Ab_c$ can be both polyclonal antibodies and $Ab_b$ and $Ab_d$ are both monoclonal antibodies. In one- and two-step sandwich immunoassays, $Ab_c$ and $Ab_d$ are preferably monoclonal antibodies.

The following examples are provided for purposes of further illustration only and are not intended to be limitations on the disclosed invention.

EXAMPLE 1

IgE Enzyme Immuno Assay (Prior Art)

Materials

Polystyrene bead coated with a monoclonal antibody directed against a specific IgE site ($Ab_b$-SC).

Horse radish peroxidase-labeled antibody directed against different IgE sites (L-$Ab_a$) and having a K of about $2 \times 10^{10}$.

o-Phenylenediamine
Hydrogen peroxide
Stopping solution
IgE Standards 0, 10, 25, 75, 200, and 400 IU/ml
Substrate buffer Protocol 1. Allow all components and samples to equilibrate to room temperature and mix well prior to use.
2. Add 20 µl standard (including zero dose or sample to each test tube.
3. Add 300 µl diluted conjugate to each tube.
4. Mix by gently shaking tube rack. Tap rack to displace air bubbles.
5. Remove bead basket from container with forceps. Hold over container until drained and place on inverted cap. Place one bead in each tube.
6. Gently shake tube rack to mix. Tap rack to remove air bubbles if necessary.
7. Incubate the tubes in a 37±1° C. water bath for 30 minutes.
8. Prepare the substrate solution during the last five minutes of the incubation. Use plastic forceps to handle tablets.
9. Wash beads by filling each tube with approximately 3 ml distilled water and aspirate. Repeat two more times.
10. At timed intervals, add 300 µl of enzyme substrate solution to each tube.
11. Shake test tube rack to ensure mixing and cover tubes to exclude light.
12. Incubate 30±1 minute at 20° C. to 25° C.
13. At timed intervals, add 1 ml Stopping Solution to each tube. Add in the same sequence and with the same timing as used for substrate addition. Mix by gentle shaking.
14. Zero the spectrophotometer against distilled water and measure the absorbance of samples and standards at 492 nm. Calculate corrected absorbances for each standard and sample by subtracting the absorbance of the reagent blank (zero dose).

Calculations

1. On semi-logarithmic graph paper, label the linear axis with absorbance (0 to 2.00A) and label the logarithmic axis with the concentration of the standards (10 to 400 IU/ml).
2. Prepare the standard curve by plotting the average corrected absorbances of the standards, and connecting the points with straight lines.
3. Use the corrected absorbances of the samples to interpolate sample concentrations from the standard curve.

The results of this experiment are set forth in Table I.

EXAMPLE 2

IgE Enzyme Immunoassay (Present Invention)

The materials, protocol, and calculations set forth in Example 1 were employed with one modification. The sole modification consisted of the use of one additional type of horseradish peroxidase-labeled antibody directed against different IgE sites (L-$Ab_c$) and having a K of about $3 \times 10^9$. The results of this experiment are also set forth in Table I.

TABLE I

| | Absorbance | |
|---|---|---|
| IgE, IU/ml | Prior Art (Example 1) | Present Invention (Example 2) |
| 0 | 0.089 | 0.126 |
| 0.161 | 0.186 | |
| 25 | 0.282 | 0.323 |
| 75 | 0.614 | 0.634 |
| 200 | 1.069 | 1.099 |
| 400 | 1.396 | 1.592 |
| 1,000 | 1.916 | 2.226 |
| 4,000 | 1.994 | 2.808 |
| 8,000 | 1.551 | 2.718 |
| 16,000 | 1.387 | 3.018 |
| 40,000 | 1.013 | 2.826 |

The IgE assays of Examples 1 and 2 have a dynamic range of from 0 to 400 IU IgE per ml. Accordingly, the data set forth in Table I indicate that at IgE concentrations greater than 8000 IU/ml, one would obtain a false negative result with the prior art procedure because of the presence of the hook effect. In contrast, with the procedure and kit of the present invention, the hook effect is avoided for IgE concentrations of at least 40,000 IU/ml. As the data of Table I also show, this avoidance is accomplished without any significant elevation of signal in the dynamic range.

EXAMPLE 3

HCG Enzyme Immuno Assay (Prior Art)

Materials

Polystyrene bead coated with a monoclonal antibody directed against a specific HCG site ($Ab_b$-SC).

Horse radish peroxidase-labeled antibody directed against different HCG sites (L-$Ab_a$) and having a K of about $8 \times 10^{10}$.

o-Phenylenediamine
Hydrogen peroxide
Stopping solution
HCG Standards 0, 10, 25, 75, 200, and 400 IU/ml
Substrate buffer

Protocol

1. Allow all components and samples to equilibrate to room temperature and mix well prior to use.
2. Add 200 μl standard (including zero dose or sample to each test tube.
3. Add 200 μl diluted conjugate to each tube.
4. Mix by gently shaking tube rack. Tap rack to displace air bubbles.
5. Remove bead basket from container with forceps. Hold over container until drained and place on inverted cap. Place one bead in each tube.
6. Gently shake tube rack to mix. Tap rack to remove air bubbles if necessary.
7. Incubate the tubes on a clinical rotor at 190±10 RPM for 45 minutes at 20° C. to 25° C.
8. Prepare the substrate solution during the last five minutes of the incubation. Use plastic forceps to handle tablets.
9. Wash beads by filling each tube with approximately 3 ml distilled water and aspirate. Repeat two more times.
10. At timed intervals, add 300 μl of enzyme substrate solution to each tube.
11. Shake test rack to ensure mixing and cover tubes to exclude light.
12. Incubate 30±1 minute at 20° C. to 25° C.
13. At timed intervals, add 1 ml Stopping Solution to each tube. Add in the same sequence and with the same timing as used for substrate addition. Mix by gentle shaking.
14. Zero the spectrophotometer against distilled water and measure the absorbance of samples and standards at 492 nm. Calculate corrected absorbances for each standard and sample by subtracting the absorbance of the reagent blank (zero dose).

Calculations

1. On semi-logarithmic graph paper, label the linear axis with absorbance (0 to 2.00A) and label the logarithmic axis with the concentration of the standards (1 to 100 mIU/ml).
2. Prepare the standard curve by plotting the average corrected absorbances of the standards, and connecting the points with straight lines.
3. Use the corrected absorbances of the samples to interpolate sample concentrations from the standard curve.

The results of this experiment are set forth in Table II.

EXAMPLE 4

HCG Enzyme Immuno Assay (Present Invention)

The materials, protocol, and calculations set forth in Example 3 were employed with one modification. The sole modification consisted of the use of one additional type of horseradish peroxidase-labeled antibody directed against different HCG sites (L-$Ab_c$) and having a K of about $2\times10^9$. The results of this experiment are also set forth in Table II.

TABLE II

| HCG, MIU/ml | Absorbance | |
|---|---|---|
| | Prior Art (Example 3) | Present Invention (Example 4) |
| 0 | 0.090 | 0.092 |
| 1 | 0.101 | 0.108 |
| 2.5 | 0.130 | 0.132 |
| 5 | 0.173 | 0.188 |
| 10 | 0.290 | 0.284 |
| 25 | 0.546 | 0.557 |
| 50 | 0.952 | 0.932 |
| 100 | 1.620 | 1.592 |
| 1000 | 3.82 | 3.855 |
| 10000 | 1.64 | 5.514 |
| 64880 | 0.66 | 4.37 |
| 128000 | 0.42 | 3.38 |

The HCG assays of Examples 3 and 4 have a dynamic range from 0 to 100 mIU HCG per ml. Accordingly, the data set forth in Table II indicate that at HCG concentrations greater than 10,000 mIU/ml, one would obtain a false negative result with the prior art procedure because of the presence of the hook effect. In contrast, with the procedure and kit of the present invention, the hook effect is avoided for HCG concentrations of at least 128,000 mIU/ml. As the data of Table II also show, this avoidance is accomplished without any significant elevation of signal in the dynamic range.

Based on this disclosure, many other modifications and ramifications will naturally suggest themselves to those skilled in the art. These are intended to be comprehended as within the scope of this invention.

Bibliography

1. U.S. Pat. No. 4,376,110
2. U.S. Pat. No. 4,244,940
3. Miles et al., *Analytical Biochemistry*, 61:209-224 (1974)
4. Uotila et al., *Journal of Immunological Methods*, 42:11-15 (1981)
5. Ng et al., *Clin. Chem.*, 29(6):1109-113 (1953)
6. Nomura et al., *Journal of Immunological Methods*, 56:13-17 (1983)
7. Miles et al., Symposium on Radioimmunoassay and Related Procedures in Clinical Medicine and Research, International Atomic Energy Agency, Vienna, Austria (1973) pp. 149-164.

The embodiments of the invention in which an exclusive property or privilege is claimed are defined as follows:

1. A one-step sandwich immunoassay for an antigenic substance (Ag) in a fluid, said immunoassay being of the type comprising:
    (a) contacting said fluid with (i) a soluble, labeled antibody (L-$Ab_a$) to said Ag and (ii) an antibody ($Ab_b$) to said Ag bound to a solid carrier (SC) to form an insoluble complex (L-$Ab_a$-Ag-$Ab_b$-SC);
    (b) separating said L-$Ab_a$-Ag-$Ab_b$-SC from said fluid and unreacted L-$Ab_a$; and
    (c) measuring either the amount of L-$Ab_a$ associated with said L-$Ab_a$-Ag-$Ab_b$-SC or the amount of unreacted L-$Ab_a$; characterized in that in step (a) said fluid is also contacted with at least one additional entity selected from the group consisting of at least one different type of soluble, labeled antibody (L-$Ab_c$) to said Ag and at least one different type of antibody ($Ab_d$) to said Ag bound to a solid carrier ($SC_1$);
wherein:
    (i) each type of L-$Ab_c$ and $Ab_d$-$SC_1$ has a lower average affinity constant (K) for said Ag than each respective K of L-$Ab_a$ and $Ab_b$-SC;

(ii) said additional entity is present in an amount sufficient to avoid a hook effect; and (iii) said $SC_1$ is selected from the group consisting of said SC, at least one different solid carrier ($SC_2$), and mixtures thereof (SC and $SC_2$).

2. The immunoassay of claim 1 wherein said additional entity is said $L\text{-}Ab_c$.

3. The immunoassay of claim 1 wherein $Ab_a$, $Ab_b$, $Ab_c$, and $Ab_d$ are each independently selected from the group consisting of monoclonal antibodies, polyclonal antibodies, and mixtures thereof.

4. The immunoassay of claim 1 wherein $Ab_a$ and $Ab_c$ are monoclonal antibodies.

5. The immunoassay of claim 4 wherein said additional entity is said $L\text{-}Ab_c$.

6. A two-step sandwich immunoassay for an antigenic substance (Ag) in a fluid, said immunoassay being of the type comprising:

(a) contacting said fluid with an antibody ($Ab_b$) bound to a solid carrier (SC) to form an insoluble complex (SC-$Ab_b$-Ag);

(b) contacting said SC-$Ab_b$-Ag with a soluble, labeled antibody ($Ab_a$-L) in order to form a complex (SC-$Ab_b$-Ag-$Ab_a$-L);

(c) separating said SC-$Ab_b$-Ag-$Ab_a$-L from unreacted $L\text{-}Ab_a$; and (d) measuring either the amount of $L\text{-}Ab_a$ associated with said SC-$Ab_b$-Ag-$Ab_a$-L or the amount of unreacted $L\text{-}Ab_a$; characterized in that in step (b) said SC-$Ab_b$-Ag is also contacted with at least one different type of soluble, labeled antibody ($L\text{-}Ab_c$);

wherein:

(i) each type of $L\text{-}Ab_c$ has a lower average affinity constant (K) for said Ag than the K of $L\text{-}Ab_a$; and (ii) said additional entity is present in an amount sufficient to avoid a hook effect.

7. The immunoassay of claim 6 wherein $Ab_a$, $Ab_b$, and $Ab_c$ are each independently selected from the group consisting of monoclonal antibodies, polyclonal antibodies, and mixtures thereof.

8. The immunoassay of claim 6 wherein $Ab_a$ and $Ab_c$ are monoclonal antibodies.

9. A direct nephelometric immunoassay for an antigenic substance (Ag) in a fluid, said immunoassay being of the type comprising:

(a) contacting said fluid with an antibody (Ab) to said Ag in order to form a complex Ab-Ag; and (b) measuring the amount of formed Ab-Ag; characterized in that in step (a) said fluid is also contacted with at least one additional type of antibody $Ab_e$;

wherein:

(i) each type of $Ab_e$ has an average affinity constant (K) for said Ag lower than the K of said Ab; and (ii) said additional entity is present in an amount sufficient to avoid a hook effect.

10. The direct nephelometric immunoassay of claim 9 wherein each additional type of $Ab_e$ is a monoclonal antibody.

11. The direct nephelometric immunoassay of claim 9 wherein each additional type of $Ab_e$ is a polyclonal antibody.

12. A reagent of the type comprising:

(a) a soluble, labeled antibody ($L\text{-}Ab_a$) to an antigenic substance (Ag); and (b) an antibody ($Ab_b$) to said Ag bound to a solid carrier (SC);

characterized in that said reagent further comprises at least one additional entity selected from the group consisting of at least one different type of soluble, labeled antibody ($L\text{-}Ab_c$) to said Ag and at least one different type of antibody ($Ab_d$) to said Ag bound to a solid carrier ($SC_1$);

wherein:

(i) each type of $L\text{-}Ab_c$ and $Ab_d$-$SC_1$ has a lower average affinity constant (K) for said Ag than each respective K of $L\text{-}Ab_a$ and $Ab_b$-SC;

(ii) said additional entity is present in an amount sufficient to avoid a hook effect when said reagent is employed in an immunoassay; and (iii) said $SC_1$ is selected from the group consisting of said SC, at least one different solid carrier ($SC_2$), and mixtures thereof (SC and $SC_2$).

13. The reagent of claim 12 wherein said $Ab_a$, $Ab_b$, $Ab_c$, and $Ab_d$ are each independently selected from the group consisting of monoclonal antibodies, polyclonal antibodies, and mixtures thereof.

14. The reagent of claim 12 wherein said $Ab_a$ and $Ab_c$ are monoclonal antibodies.

15. The reagent of claim 14 wherein said additional entity is said $L\text{-}Ab_c$.

16. The reagent of claim 12 wherein said additional entity is said $L\text{-}Ab_c$.

17. A reagent of the type comprising an antibody (Ab) to an antigenic substance (Ag), characterized in that said reagent further comprises at least one different type of antibody ($Ab_e$), wherein:

(i) each different type of said $Ab_e$ has a lower average affinity constant (K) for said Ag than the K of said Ab; and (ii) said additional entity is present in an amount sufficient to avoid a hook effect when said reagent is employed in an immunoassay.

18. The reagent of claim 17 wherein each of said $Ab_e$ is independently selected from the group consisting of monoclonal antibodies, polyclonal antibodies, and mixtures thereof.

19. The reagent of claim 18 wherein each of said $Ab_e$ is a monoclonal antibody.

20. The reagent of claim 18 wherein each of said $Ab_e$ is a polyclonal antibody.

* * * * *